(12) United States Patent  
Ferrer Ugalde et al.

(10) Patent No.: US 11,834,552 B2  
(45) Date of Patent: Dec. 5, 2023

(54) PROCESS FOR ISOLATING PHA FROM A PHA-CONTAINING BACTERIAL BIOMASS

(71) Applicant: VENVIROTECH BIOTECHNOLOGY SL, Santa Perpètua de Mogoda (ES)

(72) Inventors: Albert Ferrer Ugalde, Santa Perpètua de Mogoda (ES); Patricia Aymà Maldonado, Santa Perpètua de Mogoda (ES)

(73) Assignee: VENVIROTECH BIOTECHNOLOGY SL, Santa Perpètua de Mogoda (ES)

( * ) Notice: Subject to any disclaimer, the term of this patent is extended or adjusted under 35 U.S.C. 154(b) by 0 days.

(21) Appl. No.: 17/925,243

(22) PCT Filed: May 18, 2021

(86) PCT No.: PCT/EP2021/063184  
§ 371 (c)(1),  
(2) Date: Nov. 14, 2022

(87) PCT Pub. No.: WO2021/233935  
PCT Pub. Date: Nov. 25, 2021

(65) Prior Publication Data  
US 2023/0131006 A1 Apr. 27, 2023

(30) Foreign Application Priority Data  
May 18, 2020 (EP) .................................... 20382419

(51) Int. Cl.  
*C08G 63/89* (2006.01)  
*C08G 63/06* (2006.01)  
(Continued)

(52) U.S. Cl.  
CPC .............. *C08G 63/89* (2013.01); *C08G 63/06* (2013.01); *C08G 63/90* (2013.01); *C12P 7/625* (2013.01)

(58) Field of Classification Search  
CPC ........ C08G 63/89; C08G 63/06; C08G 63/90; C12P 7/625  
(Continued)

(56) References Cited

U.S. PATENT DOCUMENTS 8,956,835 B2 2/2015 Nakas  
10,188,773 B2 1/2019 Martin  
(Continued)

FOREIGN PATENT DOCUMENTS

EP 3205683 A1 8/2017  
EP 3152246 6/2018  
(Continued)

OTHER PUBLICATIONS

International Search Report for related patent application PCT/EP2021/063184 prepared by the European Patent Office and dated Aug. 17, 2021, in English, 3 pgs.

(Continued)

*Primary Examiner* — Fred Prince  
(74) *Attorney, Agent, or Firm* — Hassan Abbas Shakir; Shakir Law PLLC

(57) ABSTRACT

The method isolates polyhydroxyalkanoate (PHA) from a PHA-rich bacterial biomass, to the PHA isolated by the method and to a PHA having specific properties. The method treats an aqueous suspension of the PHA-rich bacterial biomass with a minimal amount of sodium hypochlorite, a methanol wash and extraction of PHA from the biomass with dimethyl carbonate (DMC).

20 Claims, 3 Drawing Sheets

(51) Int. Cl.
    *C08G 63/90* (2006.01)
    *C12P 7/625* (2022.01)
(58) Field of Classification Search
    USPC .................................................. 210/737, 729
    See application file for complete search history.

(56) References Cited

U.S. PATENT DOCUMENTS

| 2008/0299627 | A1  | 12/2008 | Kang |           |
|--------------|-----|---------|------|-----------|
| 2012/0006754 | A1* | 1/2012  | Tsai | C02F 9/00 |
|              |     |         |      | 210/713   |
| 2012/0006758 | A1* | 1/2012  | Tsai | C02F 11/13 |
|              |     |         |      | 210/756   |
| 2019/0127727 | A1* | 5/2019  | Tsai | C12N 1/06 |
| 2022/0010059 | A1* | 1/2022  | Tsai | C08G 63/78 |

FOREIGN PATENT DOCUMENTS

| WO | 1997/07229   | A1 | 2/1997  |
|----|--------------|----|---------|
| WO | 2015185024   | A1 | 12/2015 |
| WO | 2016/081902  | A1 | 5/2016  |
| WO | 2019/119157  | A1 | 6/2019  |

OTHER PUBLICATIONS

Written Opinion of the International Searching Authority for related patent application PCT/EP2021/063184 prepared by the European Patent Office and dated Aug. 17, 2021, in English, 3 pg.
Article "A Themogravimetric Analysis for Poly(3-Hydroxybutyrate) Quantification" authored by Sei Kwang Hahn and Yong Keun Chang, published in Biotechnology Techniques, vol. 9 No. 12 (Dec. 1995) p. 873-878.

* cited by examiner

A)

B)

C)

PROCESS FOR ISOLATING PHA FROM A PHA-CONTAINING BACTERIAL BIOMASS

CROSS-REFERENCE TO RELATED APPLICATIONS

This application is a national stage under 35 U.S.C. § 371 of PCT patent application PCT/EP2021/063184 filed on 18 May 2021, which is pending and which is hereby incorporated by reference in its entirety for all purposes. PCT/EP2021/063184 claims priority to European patent application 20382419.8 filed 18 May 2020, which is hereby incorporated by reference in its entirety for all purposes.

TECHNICAL FIELD

The present invention relates to a method for isolating polyhydroxyalkanoate (PHA) from a PHA-rich bacterial biomass, to the PHA isolated by said method and to a PHA having specific properties.

STATE OF THE ART

Polyhydroxyalkanoates (PHAs) are biopolyesters that include polyhydroxybutyrate (PHB), polyhydroxyvalerate (PHV), and polyhydroxyhexanoate (PHH) and copolymers of these such as poly(hydroxybutyrate-co-hydroxyvalerate) (PHBV).

PHAs have an interest from an environmental point of view as they can be obtained from renewable carbon sources and they are highly versatile polymers which can be used as replacement of petroleum-based plastics for numerous applications.

An additional value of PHAs is that they can be produced by the microbial fermentation of organic waste materials obtained from, e.g., industrial sources (such as waste streams of the food industry) or municipal sources (such as solid municipal waste or sewage sludge), helping in residue reduction. Examples of such production of PHAs have been described in, for instance, WO 2016/081902A1 and WO 2019/119157A1 which describe methods for polyhydroxyalkanoate (PHA) from organic waste.

Furthermore, PHAs are biodegradable and biocompatible.

Thus, PHAs are very attractive for their added environmental and biomedical benefits.

One of the challenges of PHA production is its recovery from the biomass in which they are produced. Methods for extracting PHA from bacterial biomass have been described in for instance WO 97/07229, which describes a process for separating polyhydroxyalkanoate (PHA) from a biomass comprising the PHA, the process comprising: (a) treating the biomass with a PHA solvent and a marginal non-solvent for PHA; (b) removing any insoluble biomass, thereby leaving behind a solution of PHA and marginal non-solvent for PHA; and (c) removing the PHA solvent from the solution, thereby resulting in a suspension of precipitated PHA in the marginal non-solvent for PHA. U.S. Pat. No. 10,188,773 describes compositions of poly-4-hydroxybutyrate (P4HB) with high purity prepared by washing P4HB biomass prior to solvent extraction, and precipitating P4HB from solution. The same solvent is preferably used to wash the P4HB biomass, and as a non-solvent to precipitate the polymer from a P4HB solvent solution. EP3152246B1 describes a method of isolation of polyhydroxyalkanoates (PHAs) from biomass fermented by microorganisms producing polyhydroxyalkanoates and/or from biomass containing at least one crop-plant producing polyhydroxyalkanoates in which polyhydroxyalkanoates are separated by extraction from biomass with an extraction agent based on chlorinated hydrocarbon, whereupon an extract is separated from the extraction solution thus obtained and, subsequently, polyhydroxyalkanoates precipitate from the extract.

However, such methods have some drawbacks, for instance the use of halogenated solvents which are undesirable from an environmental point of view, use other solvents which can require significant energy consumption for their removal or use combinations of solvents which difficult PHA recovery.

DESCRIPTION OF THE INVENTION

A first aspect of the invention relates to a method for isolating polyhydroxyalkanoate (PHA) from a PHA-rich bacterial biomass the process comprising:
a) treating an aqueous suspension of the PHA-rich bacterial biomass with a minimal amount of sodium hypochlorite sufficient to lyse the PHA-rich bacterial biomass to provide an PHA-rich biomass lysate in an aqueous phase,
b) separating PHA-rich biomass lysate from the aqueous phase,
c) washing the PHA-rich biomass lysate with water,
d) removing water from the PHA-rich biomass lysate to provide a PHA-rich biomass cake having a water content of less than 70% w/w,
e) washing the PHA-rich biomass cake with methanol to provide a PHA-rich biomass cake having a water content of less than 5% w/w,
f) optionally drying the PHA-rich biomass cake washed in step e) to provide a dry PHA-rich biomass
g) mixing the, optionally dry, PHA-rich biomass with dimethyl carbonate (DMC), to provide a suspension of PHA-rich biomass in DMC
h) heating the suspension obtained in step g) at a temperature from 70 to 90° C. for 1-3 h under vigorous stirring to provide a suspension of cell debris and a PHA-rich DMC
i) separating the cell debris from the PHA-rich DMC,
j) concentrating the PHA-rich DMC to provide a PHA-DMC concentrate
k) adding a cold non-solvent at a temperature from −20° C. to 0° C. to the PHA-DMC concentrate and mixing to provide a suspension of PHA precipitate in DMC and non-solvent
l) separating the PHA precipitate from the DMC and non-solvent
m) washing the PHA precipitate separated in step l) with cold non-solvent
n) drying the PHA precipitate washed in step m) to provide a PHA isolated from the PHA-rich bacterial biomass.

Another aspect of the invention relates to a PHA obtainable by a method as described herein.

Another aspect of the invention relates to a PHA comprising poly(3-hydroxybutyrate-co-3-hydroxyvalerate) copolymer and having a purity higher than 95%, a weight average molecular weight (Mw) of 200-500 kDa, a number average molecular weight (Mn) of 100-200 kDa, and a polydispersity index (PI) of 2-2.5.

BRIEF DESCRIPTION OF THE DRAWINGS

To complete the description and in order to provide for a better understanding of the invention, a set of drawings is provided. Said drawings form an integral part of the description and illustrate embodiments of the invention, which should not be interpreted as restricting the scope of the invention. The drawings comprise the following figures.

DETAILED DESCRIPTION OF THE INVENTION

Figure 1:
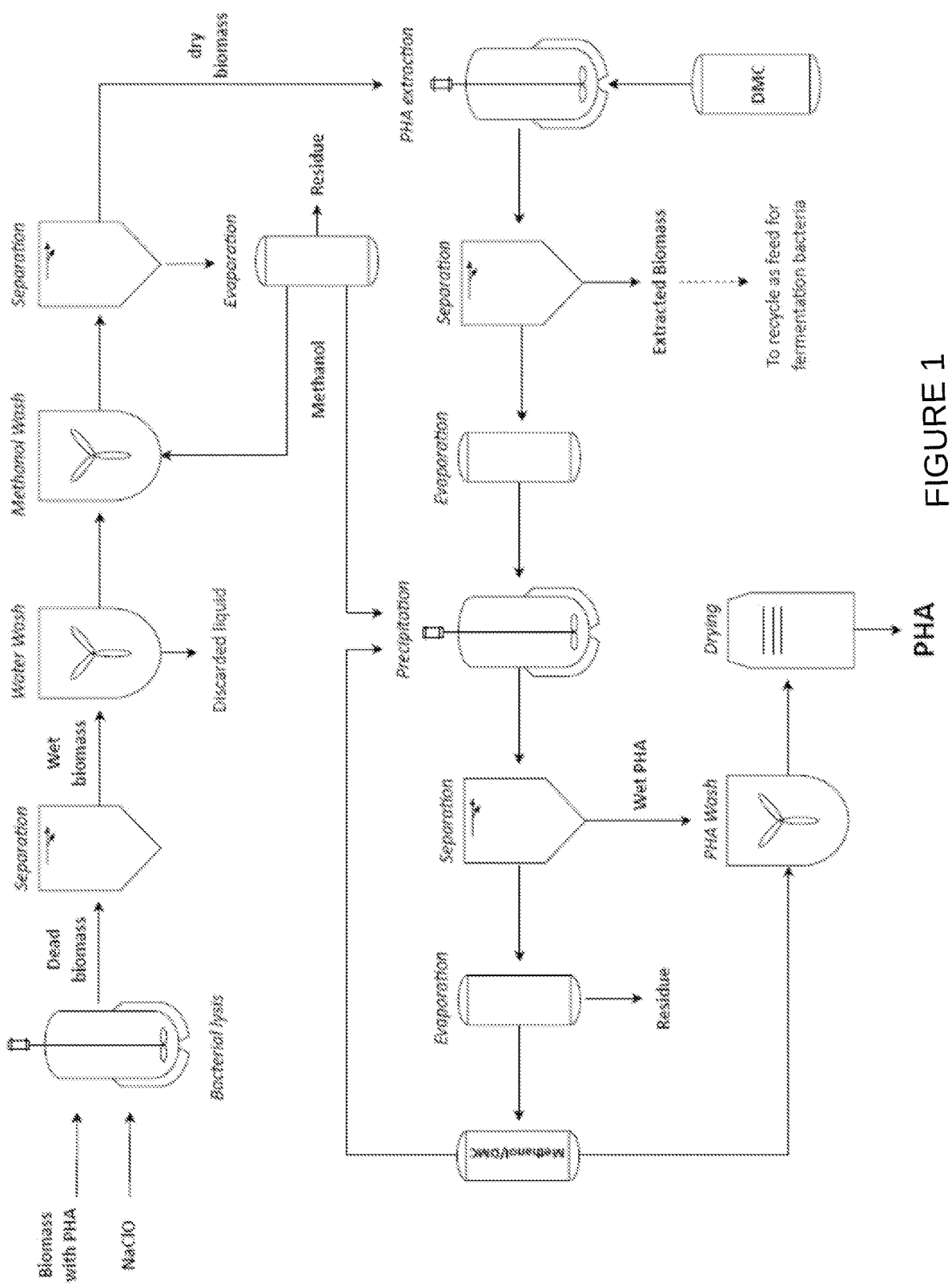
FIG. 1: shows a diagram of a method as described herein.

In a method as described herein polyhydroxyalkanoate (PHA) is isolated from a PHA-rich bacterial biomass. The method comprises treating an aqueous suspension of the PHA-rich bacterial biomass (i.e. PHA-containing bacterial biomass) with a minimal amount of sodium hypochlorite, a methanol wash and extraction of PHA from the biomass with dimethyl carbonate (DMC). Such treatments are generally performed under mild conditions (e.g. room temperature or low temperature) which advantageously ensures the quality of the extracted PHA.

The process comprises treating an aqueous suspension of the PHA-rich bacterial biomass with a minimal amount of sodium hypochlorite sufficient to lyse the PHA-rich bacterial biomass at room temperature (Step a).

The aqueous suspension of the PHA-rich bacterial biomass may be preferably obtained by fermenting an organic waste under conditions for the growth of endogenous bacteria to provide a fermented feed and for the production of PHA from said fermented feed by PHA-producing bacteria, which may preferably be also endogenous. Organic waste may be preferably selected from industrial or municipal waste streams, e.g., waste streams of the food or agricultural industry, in particular meat processing industry, milk industry or sewage sludge streams. Such conditions may generally comprise organic waste pre-treatment, organic waste fermentation, organic waste adequation, growing of (endogenous) PHA producing bacteria and accumulation of PHA in the bacteria. Generally, such fermentation may preferably comprise the pretreatment of said organic waste (e.g. by digestion of the organic waste with physical or chemical methods).

In several embodiments, organic waste may be processed in a VE-BOX, a portable technology designed by VEnvirotech Biotechnology for waste fermentation and PHA endogenous bacteria production, in order to obtain the fermented feed and further producing the PHA by said endogenous bacteria to provide an aqueous suspension of PHA-rich bacterial biomass.

In several embodiments, the aqueous suspension of PHA-rich bacterial biomass comprises a mixed culture of bacteria selected from gram-positive bacteria and gram-negative bacteria rich in PHA and unfermented organic waste in water. In particular, the mixed culture may have a higher proportion of gram-negative bacteria with respect to gram-positive bacteria. Examples of PHA producing bacteria present in a mixed culture in a PHA-rich bacterial biomass as described herein include bacilli and cocci, predominantly *Pseudomonas* s.p., *Comamonas* s.p. or *Paracoccus* s.p.

Unfermented organic waste present in an aqueous suspension of PHA-rich bacterial biomass as defined herein refers to any elements of the suspension which may be present, e.g., after fermentation of an organic waste but which elements have not been consumed during the fermentation or PHA production. Other elements that may be present in the aqueous suspension of PHA-rich bacterial biomass include, e.g., inorganic elements originally present in the organic waste and which have not eliminated, e.g. during organic waste pretreatment or organic waste adequation.

The aqueous suspension of the PHA-rich bacterial biomass, in particular a PHA-rich bacterial biomass obtained by fermenting an organic waste as described herein, may have a concentration of 7.5-15 g/L based on the solids content of PHA-rich bacterial biomass per liter of aqueous suspension, in particular 8-12 g/L, more in particular 9-11 g/L, yet more in particular about 10 g/L.

As indicated above, the aqueous suspension of the PHA-rich bacterial biomass is treated with a minimal amount of sodium hypochlorite sufficient to lyse the PHA-rich bacterial biomass. Sodium hypochlorite is used in order to kill the bacteria so they do not consume the produced PHA, which would disadvantageously lower the PHA production yield, but the amount used should be minimal not arriving to the complete digestion of the bacteria in order to avoid damaging the PHA, as it has been found that high amounts of sodium hypochlorite may degrade and lower the molecular weight of the PHA produced. Generally, the PHA-rich biomass may be treated with an amount of sodium hypochlorite from 0.01 to 0.5 grams per gram of PHA-rich biomass based on its solids content. In several embodiments from 0.03 to 0.04 grams per gram of PHA-rich biomass based on its solids content may be used. In other embodiments from 0.05 to 0.45 grams of sodium hypochlorite per gram of PHA-rich biomass based on its solids content, more in particular from 0.1 to 0.2 grams of sodium hypochlorite per gram of PHA-rich biomass based on its solids content may be used. For instance, the sodium hypochlorite may be used in the form of a 10-20% w/v aqueous solution based on grams of sodium hypochlorite per 100 mL of aqueous solution, in particular a 12-18% w/v solution and more in particular about 15% w/v solution. The sodium hypochlorite aqueous solution may be added to an amount of 0.1-3 mL to an aqueous suspension of the PHA-rich bacterial biomass, per gram of PHA-rich bacterial biomass based on its solids content. In several embodiments 0.1-0.4 mL of said sodium hypochlorite aqueous solution is used per gram of PHA-rich bacterial biomass based on its solids content, in particular from 0.13-0.3 mL, in particular from 0.15-0.25 mL, preferably about 0.2 mL of about 15% w/v sodium hypochlorite solution is used. In other embodiments, 0.5-3 mL of sodium hypochlorite aqueous solution may be used per gram of PHA-rich bacterial biomass based on its solids content, in particular 0.75-2 mL, more in particular about 1 mL, of, e.g., about 15% w/v sodium hypochlorite solution may be used.

As a mode of example for 1 L of an aqueous suspension of the PHA-rich bacterial biomass having a concentration of 10 g/L based on the solids content of PHA-rich bacterial biomass, from 2 mL to 12 mL, in particular from 5 mL to 10 mL of a 15% w/v aqueous solution of sodium hypochlorite solution may be sufficient to lyse the PHA-rich bacterial biomass.

The concentration of PHA-rich bacterial biomass can be estimated by methods known in the art. For example, the dry amount of biomass contained in a known volume of liquid may be determining by drying the biomass during twenty-four hours in an oven a 105° C. and measuring the final weight. The relationship between the weight of the dry biomass and the volume containing the biomass provides an estimate of the bacterial concentration.

Bacterial lysis may be verified by methods known in the art, e.g., by saturating 20 mL of the treated aqueous suspension is with oxygen and then supplying (e.g. 0.1 mL) of a fermented organic waste as feed to the mixture, and measuring the oxygen level over a period of over 5 minutes. If oxygen concentration remains constant, it can be confirmed that bacteria are dead (for lack of consumption of oxygen), and that lysis of the bacteria has been achieved.

Typically, upon addition of the sodium hypochlorite to the aqueous suspension of the PHA-rich bacterial biomass, lysis may be achieved after, e.g., stirring the resulting suspension at room temperature (18-25° C.) for 15-45 minutes, in particular 20-40 minutes, more in particular for about 30 minutes. Sodium hypochlorite has been found to work particularly well in a method as described herein as it can be tuned to the biomass and the PHA of interest to achieve lysis with minimal damage to PHA.

Other methods of bacterial cell lysis, such as mechanical treatments, such as bead milling, are typically difficult to escalate or only work well using high concentrations of biomass (e.g., well above 15 g/L), such as using a High Pressure Homogenizer (HPH). Further the use of heat in other methods of cell lysis may result in damaging the PHA product.

In step b) of a method as described herein, the PHA-rich biomass lysate is separated from the aqueous phase. Separating may be performed by, e.g., centrifugation at room temperature. Centrifugation may be performed for 5 to 15 minutes at 3000 to 4000 rpm, in particular about 3500 rpm and the supernatant is discarded.

In step c) the PHA-rich biomass lysate is washed with water. For instance, it may be preferably washed with 5-15 volumes of water per volume of PHA-rich biomass cake, in particular 8-12 volumes of water, more in particular about 10 volumes of water, centrifuged (e.g. under the same conditions) and the supernatant is discarded. The wash may be repeated to ensure that water soluble impurities and NaClO are removed.

In step d) water is removed from the PHA-rich biomass lysate to provide a PHA-rich biomass cake having a water content of less than 70% w/w, in particular less than 60% w/w and more in particular less than 50% w/w. For instance, the PHA-rich biomass lysate may be filtered through a filter press to provide the PHA-rich biomass cake.

In step e) the PHA-rich biomass cake is washed with methanol to provide a PHA-rich biomass cake having a water content of less than 5% w/w, in particular less than 3% w/w and more in particular less than 2% w/w. For instance, washing the PHA-rich biomass cake with methanol may be performed by I) adding to the PHA-rich biomass cake 1-10 mL of methanol per 1 g PHA-rich biomass based on its solids content, in particular 3-7 mL of methanol, and more in particular about 5 mL of methanol, II) stirring the mixture for 1-15 minutes, in particular 3-12 minutes, more in particular for 5-10 minutes, III) centrifuging the mixture and IV) discarding the supernatant, and optionally repeating steps I)-IV). The methanol wash may be preferably performed at room temperature. Such methanol wash ensures that most of the water has been removed as well as many organic impurities, such as lipids.

In several embodiments, methanol may be recovered from the washing of step e) by methods known in the art, e.g., by distillation and condensation of methanol from the supernatant. The recovered methanol may preferably re-used in a subsequent step e) and/or subsequent step l) of a method as described herein.

In optional step f) the PHA-rich biomass cake washed in step e) is dried to provide a dry PHA-rich biomass. Drying may be simply performed by, e.g., leaving the PHA-rich biomass cake open to atmosphere in order to allow most of the solvent to evaporate, e.g. for 0.5-3 h, in particular for 1-2 h. It has been found that using methanol, and in particular low amounts of methanol as described herein, advantageously favors removal of water and methanol itself without having to use highly energy consuming steps to dry the PHA-rich biomass cake which are not desirable also from an environmental point of view.

In several embodiments, the dry PHA-rich biomass obtained in step f) may generally have a total solvent content from 5-15% w/w based on the total weight amount of solvent and total weight amount of dry PHA-rich biomass, in particular the solvent content is less than 10% w/w and more preferably less than 7% w/w. The amount of total solvent may be determined by drying the PHA-rich biomass (e.g. in a stove) until a constant weight is achieved and determining the weight difference. Generally, the residual solvent may only consist in methanol.

In several embodiments, the dry PHA-rich biomass obtained in step f) may have less than 10% w/w of methanol based on the total weight amount of methanol and total weight amount of dry PHA-rich biomass, in particular less than 7% w/w of methanol, and more in particular less than 5% w/w of methanol.

It has been found that, such low amounts of residual solvents in the dry PHA-rich biomass advantageously favor the subsequent extraction of PHA from the biomass. The use of methanol as described herein has been found to be particularly successful in providing a dry PHA-rich biomass with low solvent contents. Furthermore, any residual amount of methanol has been found to be compatible with the solvent of choice for PHA extraction dimethyl carbonate (DMC).

However, step f) is entirely optional, and the PHA-rich biomass may be used without performing step f). Such PHA-rich biomass may be simply referred to as PHA-rich biomass or as wet PHA-rich biomass. Wet PHA-rich biomass may have a total solvent content from 70-95% w/w based on the total weight amount of solvent and total weight amount of PHA-rich biomass, in particular from 75-90% w/w and more in particular from 80-85% w/w. Accordingly, the wet PHA-rich biomass may have 5-30% of PHA-rich biomass based on the solids content, in particular from 10 to 25%, more in particular from 15-20%. Thus, if the optional drying step f) is not performed, the PHA-rich biomass mixed with DMC in step g) may have a solvent content from 70-95% w/w based on the total weight amount of solvent and PHA-rich biomass, in particular from 75-90% w/w and more in particular from 80-85% w/w.

In step g) the, optionally dry, PHA-rich biomass is mixed with dimethyl carbonate (DMC), to provide a suspension of PHA-rich biomass in DMC. Generally, 5-70 mL of may be used for 1 g of PHA-rich biomass based on its solid contents. In several embodiments 7.5-12.5 mL of DMC may be used for 1 g of PHA-rich biomass based on its dry contents, in particular about 10 mL. In other embodiments, 15-65 mL may be used for 1 g of PHA-rich biomass based on its solid contents, in particular 30-60 mL may be used, more in particular about 50 mL may be used.

If methanol is present in the, optionally dry, PHA-rich biomass, the volume ratio methanol to DMC (MeOH:DMC) may be, e.g., 10:0.01 to 10:0.05, or 10:0.02 to 10:0.05 e.g. about 10:0.05. Ratios in this ranges have been found to provide a good balance between the yield of extraction and economical costs.

In step h) the suspension obtained in step g) is heated at a temperature from 70 to 90° C. for 1-3 h under vigorous stirring to provide a suspension of cell debris and a PHA-rich DMC. Heating favors the extraction of PHA into DMC, turning the biomass into cell debris and is performed by methods known in the art.

In step i) the cell debris is separated from the PHA-rich DMC. Separation is preferably performed by filtration. In particular, filtration is preferably performed by filtering the suspension obtained in step h) when it is still hot, in particular at a temperature from 50-90° C. Filtration at these temperatures (hot filtration) has been found to favor the separation of the cell debris from PHA-rich DMC and in particular to avoid loss of PHA by preventing its precipitation. Higher temperatures would favor evaporation of DMC and may favor damage of PHA. Filtration is advantageous with respect to other types of separation as it is quick and allows for the suspension to be separated when still hot, which is not the case for, e.g., centrifugation which requires a lot of time and the suspension would cool down whereby PHA could start precipitating and be lost together with the cell debris.

In several embodiments the cell debris separated in step i) is dried (e.g. in an oven) and stored for later use or directly used as feed in a microbial fermentation. Drying may be performed, e.g., in an oven to remove all the solvent. For instance, the dried cell debris may be used in a fermentation to provide the aqueous suspension of PHA-rich bacterial biomass as described above.

In step j) the PHA-rich DMC is concentrated to provide a PHA-DMC concentrate. Concentrating may be performed by means known in the art by, e.g., evaporating DMC. The evaporated DMC may be recovered and re-used in, e.g., a subsequent step g) of a method as described herein.

In step k) a cold non-solvent at a temperature from −20° C. to 0° C. is added to the PHA-DMC concentrate and mixed to provide a suspension of PHA precipitate in DMC and non-solvent. The term non-solvent as used herein refers to a solvent wherein the PHA is insoluble, e.g. at insoluble at room temperature or at low temperature (e.g. of −20° C. to 0° C.).

The addition of cold non-solvent induces the precipitation of PHA.

The non-solvent may be an alcohol, an aqueous alcohol or water. The non-solvent may be preferably selected from water, methanol or ethanol, more preferably is water and/or methanol, and most preferably is methanol. The use of methanol as non-solvent advantageously facilitates the subsequent removal of the non-solvent from the PHA, both because methanol is miscible with DMC and at the same time has a low boiling point. The use of water as non-solvent may advantageously reduce the number of reagents used in the process.

The cold non-solvent is added in an amount of 7-3 mL, in particular 6-4 mL, more in particular about 5 mL, per 1 mL of PHA-DMC concentrate.

In step k) mixing may also be performed at a low temperature, in particular at a temperature from −5 to 5° C. This further facilitates PHA precipitation.

In step l) the PHA precipitate is separated from the DMC and non-solvent. For instance, the suspension of PHA precipitate in DMC and non-solvent may be filtered.

In step m) the PHA precipitate separated in step l) is washed with cold non-solvent. The non-solvent used in the wash preferably is the same non-solvent used in step k). The filtered precipitate may be preferably washed with cold non-solvent using 1-2 mL of cold non-solvent per gram of PHA.

In step j), l) and/or m) the DMC and/or non-solvent may be recovered and, preferably, the recovered DMC and/or non-solvent is re-used in a subsequent step e), when the non-solvent is methanol, a subsequent step g), a subsequent step k) and/or a subsequent step m). In the case of DMC, in a method as described herein, the amount of DMC that can be re-used is about 90% of the DMC.

Preferably the non-solvent is methanol and wherein the non-solvent is methanol and in step e), in step j), in step l) and/or in step m) methanol and/or DMC is recovered and, preferably, the recovered methanol and/or DMC is re-used in a subsequent step e), a subsequent step g), a subsequent step k) and/or a subsequent step m).

In step n) the PHA precipitate washed in step m) is dried to provide a PHA isolated from the PHA-rich bacterial biomass. For instance, the PHA may be dried in an oven at a temperature from 50-70° C., in particular at about 60° C. Drying may be performed for 6-48 h, in particular 12-36 h, more in particular for about 24 h.

The isolated PHA has a high yield of recovery. In particular, the yield of PHA recovery may be of 40-80% w/w, in particular from 50-70% w/w, more in particular of about 60% w/w, based on the weight amount of PHA per total solids content of PHA-rich bacterial biomass.

The chemical nature of the PHA may be verified by methods known in the art, in particular, using proton Nuclear Magnetic Resonance ($^1$H-NMR) and/or Gel Permeation Chromatography (GPC).

A PHA isolated in a process as described herein may comprise polyhydroxybutyrate (PHB), polyhydroxyvalerate (PHV), poly(3-hydroxymethylvalerate) (PHMV), and polyhydroxyhexanoate (PHH), and copolymers of these such as poly(hydroxybutyrate-co-hydroxyvalerate) (PHBV). In particular, the PHA may typically comprise poly(3-hydroxybutyrate-co-3-hydroxyvalerate).

A PHA isolated in a process as described herein may typically have a high purity, in particular when compared to other known processes of PHA isolation (e.g. those using mechanical and chemical digestion methods). In particular, the purity of the PHA may be greater than 90 mol %, having a lipid residue content of less than 10 mol %. In particular, a purity greater than 95 mol % is typically achieved.

The purity may be determined by known methods, in particular proton Nuclear Magnetic Resonance ($^1$H-NMR) and/or Thermogravimetric analysis (TGA).

$^1$H-NMR may be typically performed by dissolving a sample of the polymer in deuterated chloroform ($CDCl_3$) in a, e.g., 250 MHz Bruker spectrometer.

TGA may be performed as described by, e.g., Kwang Hahn and Keun Chang in "A Thermogravimetric Analysis for Poly(3-Hydroxybutyrate) Quantification" in Biotechnology Techniques, Volume 9 No. 12 (December 1995) p. 873-878.

A PHA isolated in a process as described herein may typically have a weight average molecular weight (Mw) of 200-500 kDa, a number average molecular weight (Mn) of 100-200 kDa, and a polydispersity index (PI) of 2-2.5.

The Mw and Mn can be determined by Gel Permeation Chromatography (GPC) using, e.g., an Agilent 1260 Infinity II chromatograph equipped with one Agilent PLgel 5 μm Guard 50×7.5 mm guard column and two Agilent PLgel 5 μm Mixed-C 300×7.5 mm columns. Clear PHBV solutions with a concentration of 5 mg mL-1 were prepared by dissolving 50 mg of the copolymer into 10 mL of chloroform. A sample injection volume of 100 μL was used, and the analysis was performed at 30° C., with flow rate of chloroform (as eluent) set to 1.0 mL min-1. Average molecular weights of the polymer were calculated based using polystyrene standards.

The PI is calculated by dividing the determined Mw by the determined Mn (PI=Mw/Mn).

A PHA isolated in a process as described herein may typically have a melting temperature of 150 to 180° C., in particular from 155 to 170° C. and more in particular from 160-165° C. as determined, e.g., by differential scanning calorimetry (DSC) and a degradation temperature from 250 to 280° C., in particular from 255 to 270° C., more in particular from 260 to 265° C. determined by thermogravimetric analysis (TGA).

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention is illustrated by the following examples without being limited hereto or thereby.

Example 1

In this example 10 litres of biomass were processed having an estimated concentration of 10 g/L (which would imply a total weight of dry biomass of 100 grams, i.e., solids content). To ensure bacterial death, 20 mL of an aqueous solution of sodium hypochlorite (NaClO) 15% w/w are added, i.e. 2 mL NaClO/l of biomass. The suspension was stirred at room temperature for 30 minutes and then bacterial lysis was verified by saturating of the treated aqueous suspension with oxygen and then supplying (2-3 mL) of a fermented organic waste as feed to the mixture, and measuring the oxygen level over a period of 5 minutes. The oxygen concentration remained constant and therefore it was confirmed that bacteria were dead and that lysis of the bacteria had been achieved.

The biomass suspension was subsequently centrifuged for 10 minutes at 3500 rpm at room temperature, and the supernatant was discarded. Then, biomass was washed with 1 L of water and centrifuged twice, always discarding the supernatant. In this manner, it was ensured that the majority of NaClO and water-soluble impurities were removed. The biomass was filtered through a filter press to remove the maximum amount of water, reducing the water content in the biomass cake to less than 70%.

Posteriorly, the biomass was washed by stirring it with a minimum amount of methanol, 500 mL, for 10 minutes and posteriorly centrifuged, discarding again the supernatant. This operation was repeated one more time to ensure that most of the water had been removed as well as many organic impurities. The water content at the end of the treatment was less than 5%, as determined by $^1$H-NMR. Finally, biomass was left open to atmosphere inside a fume hood for two hours in order to allow most of the solvent to evaporate.

A 2-litre round-bottomed flask incorporating a magnetic stirrer was loaded with the pretreated biomass and 1000 mL of dimethyl carbonate, forming a suspension. A condenser was attached to the neck of the flask to prevent solvent loss and the mixture was then heated using a hot plate equipped with a Heat-On block adapter for round-bottomed flasks.

The extraction temperature with DMC was 80° C. for 2 hours under vigorous stirring. Then, the hot mixture was filtered through filter paper, obtaining a DMC filtrate which contains the polymer, whereas the precipitate that remains on the filter mainly corresponds to cell debris, which was dried and stored as feed for fermentation bacteria. Then, the filtrate was concentrated in a rotary evaporator to a volume of 100 mL and the evaporated DMC (700-800 mL) was recovered and kept for following extraction cycles.

500 mL of cold non-solvent (methanol or ethanol) were added over the DMC concentrate to induce the precipitation of the polymer, and the resulting suspension was filtered under vacuum through a sintered filter glass. The polymer was then washed twice with cold non-solvent and left to dry for an hour at room temperature while the mother liquor was concentrated in a rotary evaporator to recover the maximum amount of non-solvent (normally around 400 mL) for successive extractions.

Finally, the polymer was left in the oven to dry at 60° C. for 24 hours. The recovery yield was of 50% w/w.

Figure 2:
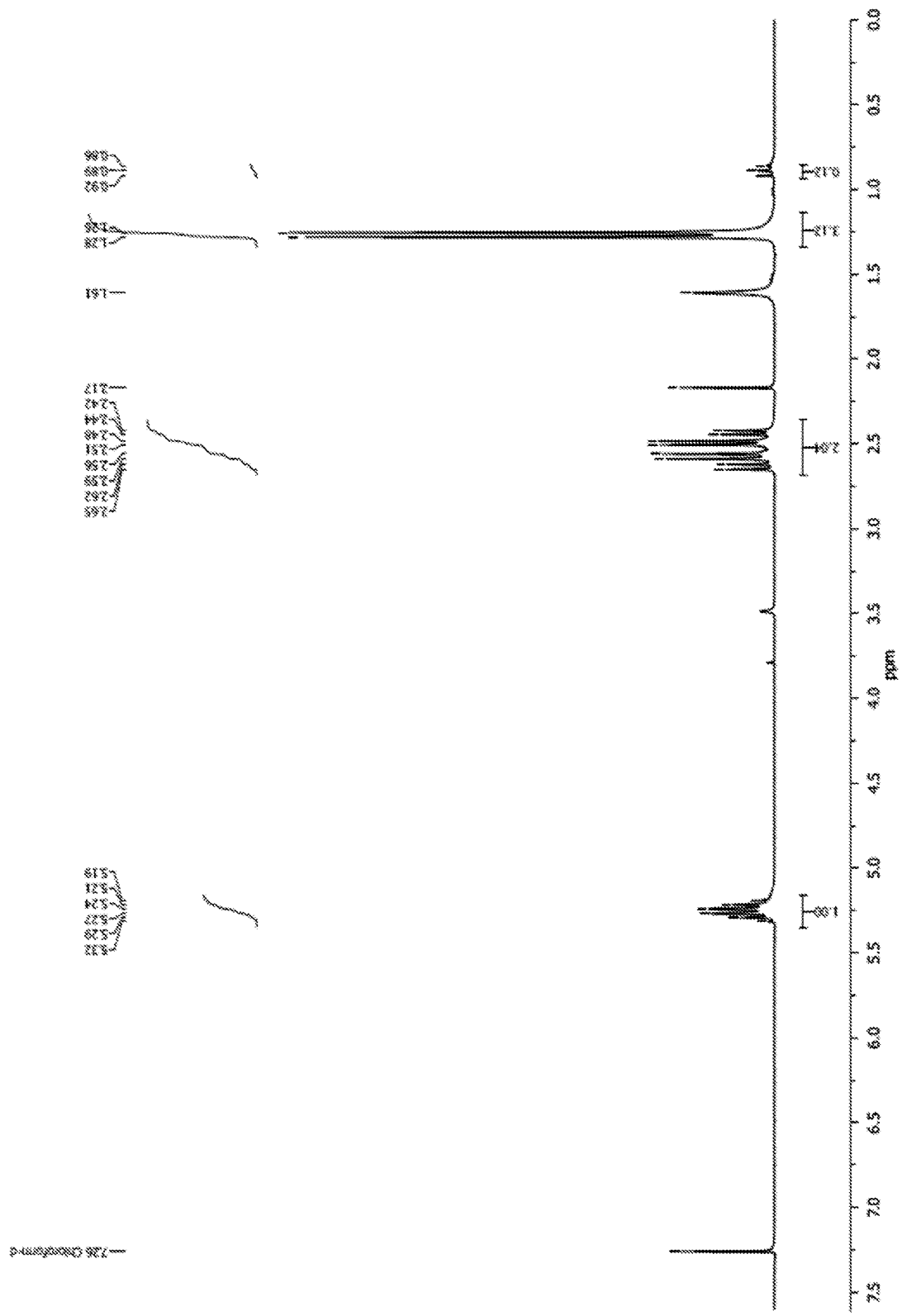
FIG. 2: $^1$H-NMR of the isolated PHA of Example 1

The structure of the polymer, was confirmed to be a co-polymer of P(3HB-co-3HV) is by using proton Nuclear Magnetic Resonance ($^1$H-NMR) RMN, using a sample of 20 mg of isolated PHA dissolved in CDCl$_3$ in a 250 MHz Bruker spectrometer. The $^1$H-NMR of the isolated PHA is shown in FIG. 2.

Figure 3:
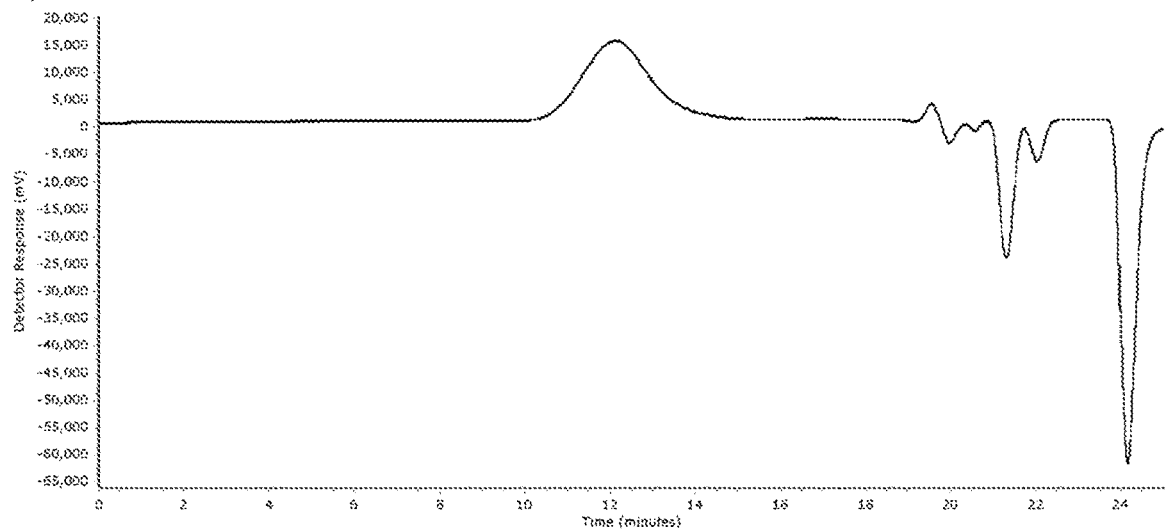
FIG. 3: GPC analysis and TGA of the isolated PHA of Example 1: A) chromatogram plot and B) distribution plot; C) TGA.
Figure 3:
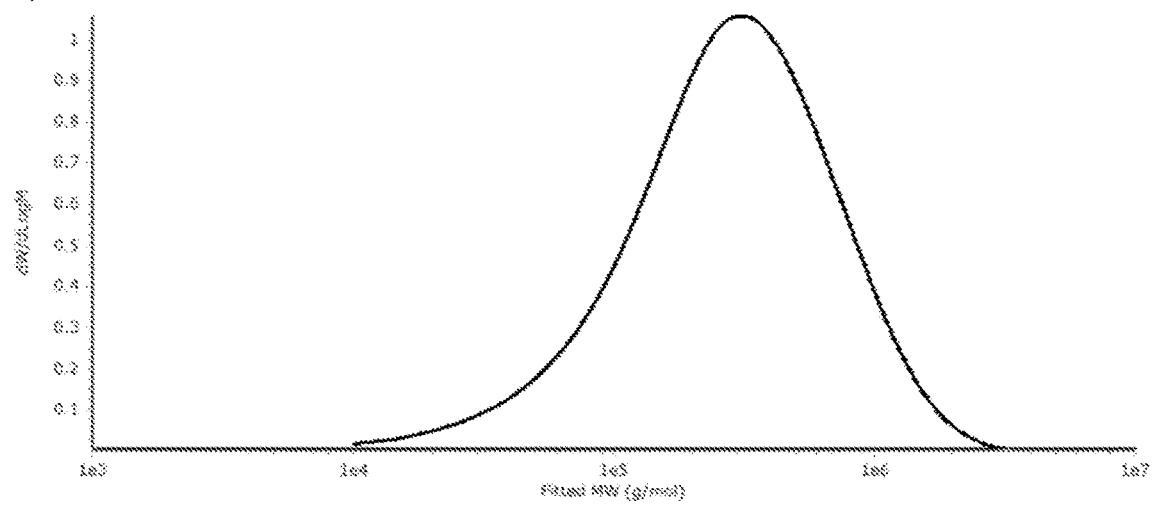
Figure 3:
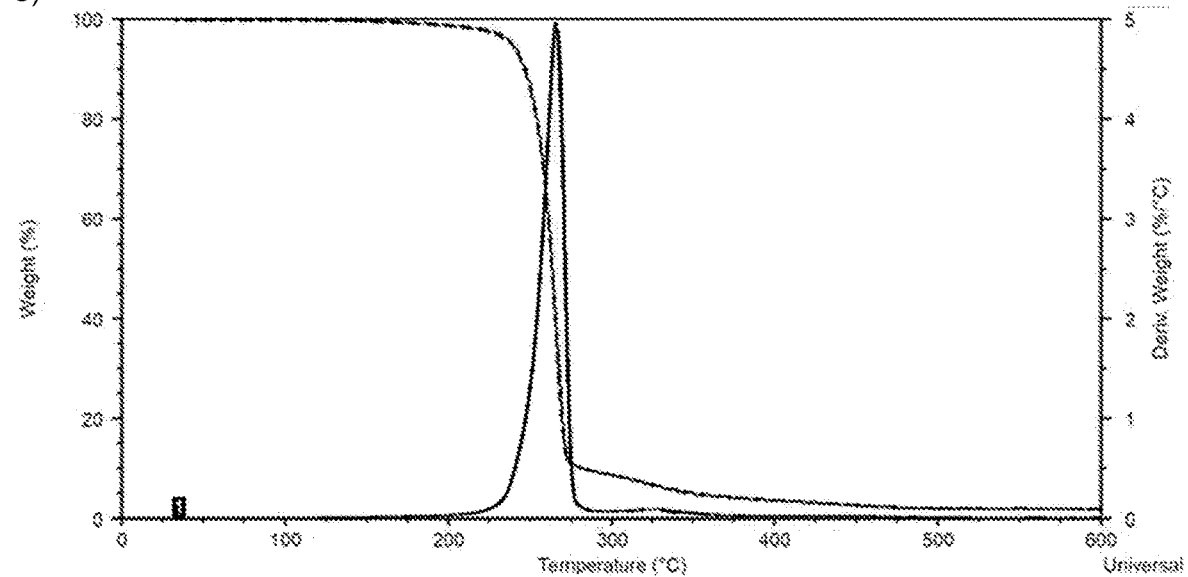

The isolated PHA had a purity greater than 95% (as verified by TGA), a Mw of 391 KDa, an Mn of 164 KDa and a PI of 2.38 as determined by GPC. The chromatogram plots and distribution plots of the GPC are presented in FIG. 3 as A) and B) respectively and the TGA in FIG. 3 C).

Example 2

In this example 10 litres of biomass were processed having an estimated concentration of 10 g/L (which would imply a total weight of dry biomass of 100 grams, solids content). To ensure bacterial death, 100 mL of an aqueous solution of sodium hypochlorite (NaClO) 15% w/w are added, i.e., 10 mL NaClO/l of biomass. The suspension was stirred at room temperature for 30 minutes and then bacterial lysis was verified by saturating of the treated aqueous suspension with oxygen and then supplying (2-3 mL) of a fermented organic waste as feed to the mixture, and measuring the oxygen level over a period of 5 minutes. The oxygen concentration remained constant and therefore it was confirmed that bacteria were dead and that lysis of the bacteria had been achieved.

The biomass suspension was subsequently centrifuged for 10 minutes at 3500 rpm at room temperature, and the supernatant was discarded. Then, biomass was washed with 1 L of water and centrifuged twice, always discarding the supernatant. In this manner, it was ensured that the majority of NaClO and water-soluble impurities were removed. The biomass was filtered through a filter press to remove the maximum amount of water, reducing the water content in the biomass cake to less than 70%.

Posteriorly, the biomass was washed by stirring it with a minimum amount of methanol, 500 mL, for 10 minutes and posteriorly centrifuged, discarding again the supernatant. This operation was repeated one more time to ensure that most of the water had been removed as well as many organic impurities. The water content at the end of the treatment was less than 5%, as determined by $^1$H-NMR. The total solvent content of the biomass was 85-80% w/w.

A 2-litre round-bottomed flask incorporating a magnetic stirrer was loaded with the pretreated biomass and 1000 mL of dimethyl carbonate, forming a suspension. A condenser was attached to the neck of the flask to prevent solvent loss and the mixture was then heated using a hot plate equipped with a Heat-On block adapter for round-bottomed flasks.

The extraction temperature with DMC was 90° C. for 1 hour under vigorous stirring. Then, the hot mixture was filtered through filter paper, obtaining a DMC filtrate which contains the polymer, whereas the precipitate that remains on the filter mainly corresponds to cell debris, which was dried and stored as feed for fermentation bacteria. Then, the filtrate was concentrated in a rotary evaporator to a volume of 100 mL and the evaporated DMC (700-800 mL) was recovered and kept for following extraction cycles.

500 mL of cold non-solvent (methanol) were added over the DMC concentrate to induce the precipitation of the polymer, and the resulting suspension was filtered under vacuum through a sintered filter glass. The polymer was then washed twice with cold non-solvent and left to dry for an hour at room temperature while the mother liquor was concentrated in a rotary evaporator to recover the maximum amount of non-solvent (normally around 400 mL) for successive extractions.

Finally, the polymer was left in the oven to dry at 60° C. for 24 hours. The recovery yield was of 50% w/w.

The structure of the polymer, was confirmed to be a co-polymer of P(3HB-co-3HV) is by using proton Nuclear Magnetic Resonance ($^1$H-NMR) RMN, using a sample of 20 mg of isolated PHA dissolved in $CDCl_3$ in a 250 MHz Bruker spectrometer. The $^1$H-NMR of the isolated PHA is not shown.

The isolated PHA had a purity greater than 95% (as verified by TGA), a Mw of 391 KDa, an Mn of 164 KDa and a PI of 2.38 as determined by GPC.

What is claimed is:

1. A method for isolating polyhydroxyalkanoate (PHA) from a PHA-containing bacterial biomass, the method comprising the steps of:
   (a) treating an aqueous suspension of the PHA-containing bacterial biomass with a minimal amount of sodium hypochlorite sufficient to lyse the PHA-containing bacterial biomass at a room temperature to provide a PHA-containing biomass lysate in an aqueous phase;
   (b) separating the PHA-containing biomass lysate from the aqueous phase;
   (c) washing the PHA-containing biomass lysate with water;
   (d) removing water from the PHA-containing biomass lysate to provide a PHA-containing biomass cake having a water content of less than 70% w/w;
   (e) washing the PHA-containing biomass cake with methanol to provide a PHA-containing biomass cake having a water content of less than 5% w/w;
   (f) mixing the PHA-containing biomass cake with dimethyl carbonate (DMC) to provide a suspension of PHA-containing biomass in DMC;
   (g) heating the suspension of PHA-containing biomass in DMC obtained in step (f) at a temperature from 70° C. to 90° C. for 1-3 hours under vigorous stirring to provide a suspension of cell debris and a PHA-containing DMC;
   (h) separating the cell debris from the PHA-containing DMC;
   (i) concentrating the PHA-containing DMC to provide a PHA-DMC concentrate;
   (j) adding a non-solvent at a temperature from −20° C. to 0° C. to the PHA-DMC concentrate and mixing to provide a suspension of a PHA precipitate in DMC and the non-solvent:
   (k) separating the PHA precipitate from the DMC and the non-solvent;
   (l) washing the PHA precipitate separated in step (k) with the non-solvent at the temperature from −20° C. to 0° C.; and
   (m) drying the PHA precipitate washed in step (l) to provide a PHA isolated from the PHA-containing bacterial biomass.

2. The method of claim 1, wherein the aqueous suspension of PHA-containing bacterial biomass is obtained
   by selecting an organic waste from waste streams of a food industry or an agricultural industry or sewage sludge, and
   by subjecting the organic waste to conditions for growth of endogenous bacteria to provide a fermented feed and for a production of PHA from the fermented feed by endogenous PHA-producing bacteria to provide the aqueous suspension of the PHA-containing bacterial biomass.

3. The method of claim 1, wherein the aqueous suspension of the PHA-containing bacterial biomass obtained has a concentration of PHA-containing bacterial biomass of 7.5-15 g/L based on a solids content of PHA-containing bacterial biomass per liter of the aqueous suspension.

4. The method of claim 1, wherein the aqueous suspension of PHA-containing bacterial biomass comprises a mixed culture of bacteria selected from gram-positive and gram-negative bacteria containing PHA and unfermented organic waste in water.

5. The method of claim 1, wherein in step (a) the PHA-containing biomass is treated with an amount of sodium hypochlorite from 0.03 to 0.04 per gram of PHA-containing biomass based on a solids content.

6. The method of claim 1, wherein in step (a) the sodium hypochlorite is a 10-20% w/v aqueous solution based on grams of sodium hypochlorite per 100 mL of the aqueous solution.

7. The method of claim 6, wherein in step (a) 0.1-3 mL of sodium hypochlorite solution is used per gram of PHA-containing bacterial biomass based on a solids content.

8. The method of claim 1, wherein in step (e) washing the PHA-containing biomass cake with methanol is performed by
   adding to the PHA-containing biomass cake 1-10 mL of methanol per 1 g PHA-containing biomass based on its solids content to obtain a first mixture,
   stirring the first mixture for 1-15 minutes,
   centrifuging the first mixture, and
   discarding a supernatant of the first mixture.

9. The method of claim 1, subsequent to step (e) comprising a step (n) of
   drying the PHA-containing biomass cake washed in step (e) to provide a dry PHA-containing biomass cake, and
   wherein in step (f) the PHA-containing biomass cake is the dry PHA-containing biomass cake of step (n).

10. The method of claim 9, wherein step (n) is performed and the dry PHA-containing biomass obtained in step (n) has a total solvent content from 5-15% w/w based on the total weight amount of solvent and total weight amount of the dry PHA-containing biomass.

11. The method of claim 10, wherein the total solvent content is less than 10% w/w.

12. The method of claim 10, wherein the dry PHA-containing biomass obtained in step (n) has less than 10% w/w of methanol based on the total weight amount of methanol and total weight amount of the dry PHA-containing biomass.

13. The method of claim 12, wherein the dry PHA-containing biomass obtained in step (n) has less than 7% w/w of methanol.

14. The method of claim 1, wherein step (n) is not performed and the PHA-containing biomass mixed with DMC in step (f) has a solvent content from 70-95% w/w based on the total weight amount of solvent and PHA-containing biomass.

15. The method of claim 1, wherein in step (h) the cell debris is separated from the PHA-containing DMC by filtering the suspension obtained in step (g) when it is still hot.

16. The method of claim 1, wherein in step (j) mixing is performed at a low temperature.

17. The method of claim 1, wherein in step (j) the non-solvent is selected from the group of water, methanol, and ethanol.

18. The method of claim 1, wherein in step (i) the separated cell debris is dried and stored for later use or directly used as feed in a microbial fermentation.

19. The method of claim 1, wherein the non-solvent is methanol and wherein in step (e), in step (i), in step (k), or in step (l) methanol or DMC is recovered.

20. The method of claim 19, wherein the recovered methanol or DMC is re-used in a subsequent step (e), a subsequent step (f), a subsequent step (j), or a subsequent step (l).

* * * * *